United States Patent [19]

Knowles

[11] Patent Number: 5,048,347

[45] Date of Patent: Sep. 17, 1991

[54] METHOD FOR TESTING CORRUGATED MEDIUM

[75] Inventor: Jonathan C. Knowles, Toledo, Oreg.

[73] Assignee: Georgia-Pacific Corporation, Atlanta, Ga.

[21] Appl. No.: 578,823

[22] Filed: Sep. 7, 1990

[51] Int. Cl.[5] ............................................. G01N 3/08
[52] U.S. Cl. ..................................................... 73/821
[58] Field of Search ........................... 73/821, 818, 819

[56] References Cited

U.S. PATENT DOCUMENTS

| | | | |
|---|---|---|---|
| 2,645,937 | 7/1953 | Skalmusky | 73/821 |
| 3,263,495 | 8/1966 | Ostrowski | 73/821 |
| 3,347,091 | 10/1967 | Cymmer et al. | 73/860 |
| 4,446,743 | 5/1984 | Gunderson | 73/822 |

FOREIGN PATENT DOCUMENTS 589073 12/1959 Canada .

OTHER PUBLICATIONS

*Testing Methods and Instruments for Corrugated Board*, Chapter 4, pp. 31-34; Hakan Markstrom, "Measurement of the In-Plane Compression Strength of Liner and Fluting Medium", ISBN 91-7970-454-9.

Primary Examiner—Jerry W. Myracle
Attorney, Agent, or Firm—Banner, Birch, McKie & Beckett

[57] ABSTRACT

The invention involves a method for testing corrugated materials, in particular, boxboard. The test involves securing a sample horizontally between jaws having a mating corrugated gripping surface profile.

3 Claims, 1 Drawing Sheet

METHOD FOR TESTING CORRUGATED MEDIUM

FIELD OF THE INVENTION

The invention involves an apparatus and method for testing wood fiber containing corrugated materials such as boxboard.

DESCRIPTION OF RELATED TECHNOLOGY

Paper is increasingly becoming the material of choice for many applications requiring structural integrity, low weight, and economic fabrication. Typically, varying combinations of flat liner and corrugated paper (cardboard) layers are made into corrugated board and corrugated boxboard. The materials used to make boxboard are predominantly wood fibers with one or more additives. These materials are made as flat sheets from a wood fiber slurry that has been laid onto a moving web. During the laying process, speed differences between the web and the fiber slurry induce a fluid shear force that can orient most of the fibers into a direction parallel to the travel path of the web. This orientation is commonly referred to as the "machine" direction. The perpendicular direction is the "cross" direction.

The in-plane compression strengths of the liner and corrugated layers are strongly related to the strength of the board or box structure made from combinations of these materials. Accordingly, test for measuring the strength of these materials must be closely scrutinized for errors. The tests must also be checked to ensure that the measured property is an accurate measure of the material strength unaffected either beneficially or detrimentally by other factors such as creep, buckling, or unintended external reinforcing. Buckle is nonplanar movement because the edge of the sample is exposed and unsupported. Creep will underestimate the actual strength of the material as either the sample or the fibers travel in the direction of the applied force rather than failing. Creep is a sample or fiber movement in the plane of the compression. Buckle will similarly underestimate material strength due to the appearance of a moment force on the sample. Buckling of even 2% will render the strength readings meaningless.

To date, a number of testing methods have been used for testing paper medium. See, Markström, "Chapter 4—Measurement of the In-plane Compression Strength of Liner and Fluting Medium", *Testing Methods and Instruments for Corrugated Boards*, pp. 31–34 for a description of the various testing methods and an explanation of the physics associated with testing cardboard materials. This section of the publication is herein incorporated by reference.

The CLT (concora liner test) method requires a corrugated sample measuring 0.5 inches by 6 inches with the fibers running along the 6 inch length of the sample (the "machine direction"). The flutes run across the 0.5 inch width of the sample. The measured value is taken by positioning the sample between two flat, horizontal platens and applying pressure vertically until the flutes collapse. The measured values is known as the "flat crush resistance" of the corrugated sample.

A standard method for testing the crush strength of corrugated medium is with the Corrugated Crush Test (CCT) which is described in U.S. Pat. Nos. 589,073 and 3,263,495. This test cuts a 0.5"×3"or 6"sample strip in the machine direction (fibers parallel to the long edge of the sample), flutes the strip, and clamps the corrugated strip vertically in a fluted jig so that 0.25"extends upwardly from the top of the jig. Force is applied downwardly on the extended edge until the sample fails. The CCT method, however, suffers from a vulnerability to creep and buckle due to the unsupported edge.

Maintaining a parallel orientation between the top edge of the sample and the bottom is also difficult in the CCT method. Because these crush strength readings are on the order of several ounces, any nonlinear contact between the press and the sample will form uneven pressure points that result in an inaccurate reading. Moreover, any attempts to use a sample holder on top of the extended edge will apply a vertical pressure to the sample that could prematurely stress or bend the sample and introduce a source of error in the test.

The SCT method, the "short compression test", which was developed at the Swedish Pulp and Paper Research Institute (STFI) is a test for flat stock that purports to be a more accurate measure of the true fiber strength associated with fiber-based materials. The SCT was specifically developed to measure the pure crush strength of fibers in a flat sample unobstructed by external influences such as corrugation. The sample for SCT is flat and 15 mm wide by at least 6 in. long. In contrast to the CCT, the fibers run across the narrow 15 mm width of the sample so pressure is applied down the fiber length.

The sample is tested by securing the sample vertically over its entire width between a fixed jaw and a movable jaw separated by a short span of 0.7 mm. The movable jaw is forced toward the fixed jaw with a measured force until compressive failure occurs in the sample. The relatively short distance between the jaws is intended to prevent buckling and result in a true measure of fiber strength. The clamping support across the sample width eliminates edge effects.

Although the SCT method is useful for flat stock, the resulting measurement of strength does not account for the stresses induced in the material during the converting and end use processes. Boxes and other structural members are not made of flat medium; at least one layer is corrugated. During the corrugation process, medium is subject to large tensile loads in the machine direction, but Z-direction stresses can reduce caliper by as much as 30%. By some accounts, machine direction compressive strength is reduced by about 35% and cross direction compressive strength is reduced by about 20% due to the corrugation process. The result is an overall reduction by about 7% in the combined board edge crush test strength due to fluting shear stresses.

The industry needs a reliable method for accurately measuring the material strength of corrugated wood fiber-based medium. Such a process is particularly needed for boxboard where the wood fibers are oriented predominantly in one direction.

SUMMARY OF THE INVENTION

It is an object of the invention to provide a process for measuring the wood fiber strength of corrugated wood fiber-based medium that eliminates creep and buckle error that might be caused by vertical compression of the sample.

It is another object of the invention to provide a testing process that can be used in the laboratory for predicting the crush strength of materials made from corrugated wood fiber-based medium.

In accordance with the objects noted above and others that will become apparent from the description contained herein, the process according to the invention comprises:

(a) forming corrugations in a sample of wood fiber-based medium exhibiting a rectangular shape of a pair of short edges and a pair of long edges and having the fibers of said medium running substantially parallel to said long edges;

(b) placing the corrugated sample horizontally across a gap of about 0.7 to about 1 mm between a first sample holder and a second sample holder wherein each of the sample holders comprises a corrugated upper jaw in close mating relationship with both a corrugated bottom jaw and the corrugations in said sample;

(c) securing said sample in said first holder and said second holder;

(d) applying a horizontal crushing force on said sample by forcing one of said sample holders to move toward the other sample holder; and (e) measuring the force required to cause crushing failure in said sample.

The present process accurately measures the material strength in corrugated medium. The result is an accurate reading of actual strength of corrugated media. The resulting test information will permit corrugated structure designers to determine proper dimensions and optimize materials with a high degree of accuracy. Such accuracy translates into direct economic and environmental benefits.

DETAILED DESCRIPTION

Figure 1:
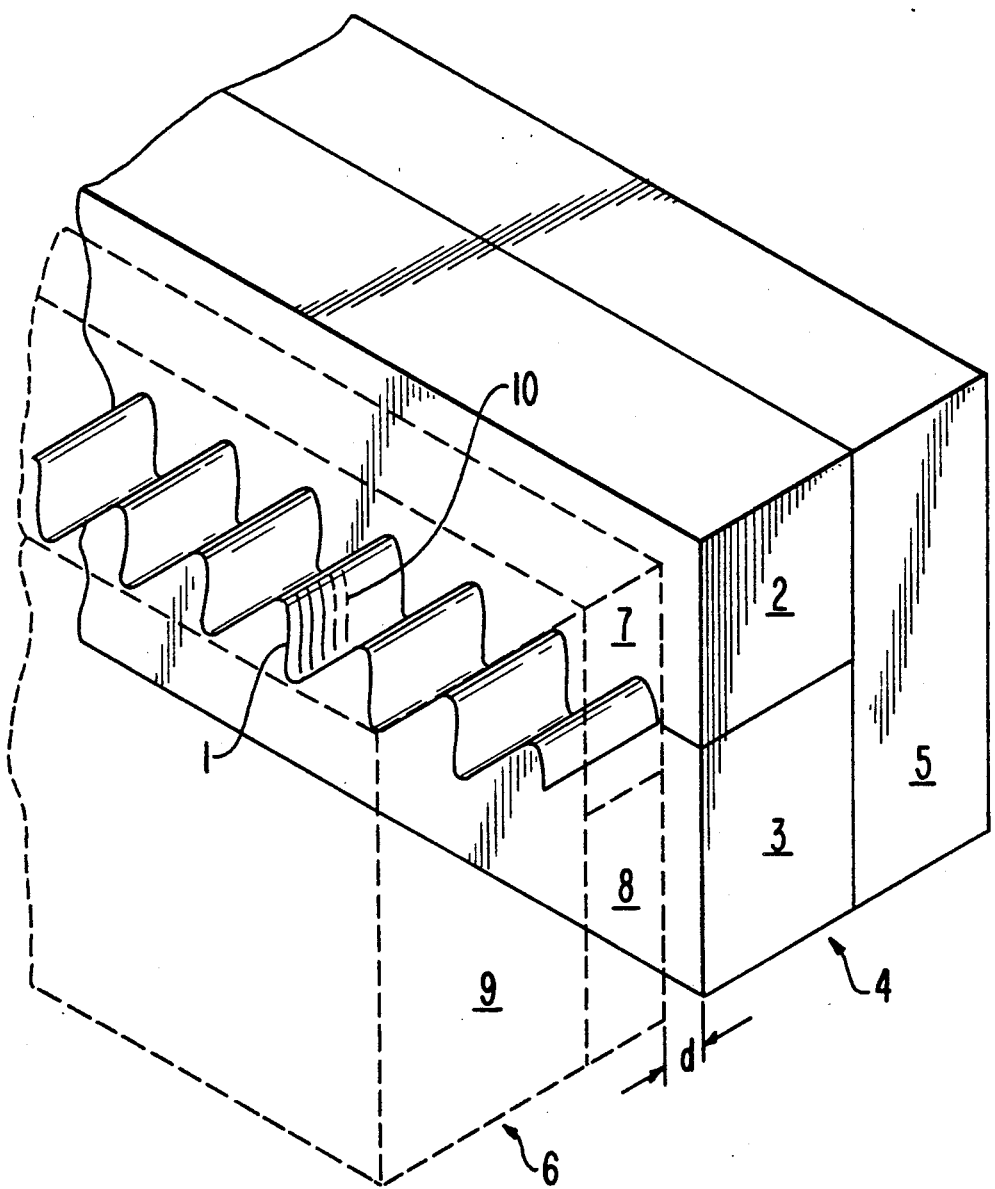
FIG. 1 is a sketch of a sample holder gripping a sample according to the invention.

The invention involves a method for testing corrugated wood-fiber containing materials that are used in a corrugated or fluted shape for load-bearing articles. As used herein, the terms "corrugated" and "fluted" are used interchangeably to denote the same essential shape. In particular, the invention is useful for testing boxboard and other paper-based products or other products having fibers oriented in predominantly one direction. Corrugated boxboard material is a particularly preferred material for testing with the process of the invention.

The sample to be tested according to the process of the invention, the Toledo Fluted Crush Test (TFCT), is first removed from bulk stock as a rectangular piece of material. Conventional sample presses with a high degree of dimensional accuracy can be used to obtain the desired sample. Preferred dimensions are 0.5"×3" with the fibers running in the machine direction (substantially parallel to the 6"dimension). When corrugated, the wood fibers will run cross direction (substantially perpendicular to the direction of the corrugations).

The sample should be prepared by taking the sample from flat stock and corrugating the removed sample. The sample should be formed with ridges and valleys having a profile as close as possible to the profile to be used in the final structure and similarly close forming conditions. The conditions will typically include combinations of heat and humidity that cause the wood fibers to be amenable to fluting. Most boxboard forming processes will apply liner materials to either side of the fluted layer thereby freezing the fluted structure in position. Accordingly, the present testing process seeks the structural information of the fluting that exists shortly after the fluting process. The sample should be fluted and then quickly (within about 6–12 seconds) laid into a sample holder assembly and tested.

The sample holder assembly comprises first and second sample holders disposed in a spaced apart, parallel relationship on a horizontal plane. The spacing between the sample holders is about 0.7–1.0 mm. Each sample holder comprises a corrugated upper half and a corrugated bottom half in a close mating relationship so that when closed, the upper and lower halves will close tightly on the corrugated sample without affecting the shape of the sample corrugation. The tightness of the fit is important for eliminating creep and buckle during the actual testing.

In addition to the tightness of the gripping action, the sample holder is preferably shaped to provide a vertically extended abutment or stop surface along the entire length of both long edges of the sample (parallel to the wood fiber orientation) of the sample. Such an abutment will ensure that the sample does not move during the compression process. These abutment surfaces should be as close to parallel to each other as practical and remain in a parallel alignment so that the sample does not move out of alignment during the test.

The corrugated sample is placed between the holders across a short gap formed therebetween and is gripped between the upper and lower portions of each holder. The sample holders are then forced together to apply crushing forces to either or both sample holders. It is preferred to have one sample holder in a fixed position attached to a conventional load cell. The other sample holder forced toward the fixed holder in a linear path.

Means for guiding the sample holders may be used to ensure parallel relative movement of the sample holders. Suitable guiding means include pin or rod guides extending between the sample holders. Also suitable are wheels or bearings on the bottom of the sample holders to facilitate sample holder displacement with a negligible amount of friction. A preferred guide is incorporated with the means used to exert the horizontal crushing force and comprises at least two parallel push rods acting against the mobile sample holder.

A number of sample holders can be used to perform the function of gripping the sample during the compression process. The preferred sample testing assembly is a modified tester made by Swedish Pulp and Paper Research Institute (STFI) for testig with the SCT method. That test apparatus includes a fixed jaw and a mobile jaw which hold a flat sample of standardized dimensions in a vertical plane. The fixed jaw is connected to a load cell for measuring the crushing load exerted on the sample and a microprocessor for converting the load readings to strength readings.

In the present invention, the STFI jaws would be replaced with jaws which allow for the sample to be tested in a horizontal orientation, gripped between mating fluted surfaces, and restrained from horizontal movement by having each long edge abut a vertically extended stop surface. The opposing stop surfaces would be as parallel as practical.

The crushing direction is important to obtain an accurate measurement of the strength of the corrugated material. In the present invention, the horizontal force is transmitted down the flutes and cross direction to the fibers. The resulting crushing pressure is, therefore, an accurate measure of the intrinsic fiber resistance and material rigidity of the corrugated sample. Suitable crushing forces increase gradually from no pressure to a top pressure of about 30 to about 130 psi depending on the thickness of the sample.

A perspective diagram of a gripped sample is shown in FIG. 1. In that figure, corrugated sample 1 is held between upper fixed jaw 2 and corrugated fixed lower jaw 3 in fixed holder 4. Sample 1 also extends across jaws 2 and 3 to abut stop 5.

Movable holder 6 (in hatched lines) includes similar elements and is spaced apart from fixed holder 4 by a distance, d, of about 0.7 to about 1 mm. Sample 1 is gripped in holder 6 between movable holder lower jaw 7 and movable holder upper jaw 8. Sample 1 extends across jaws 7 and 8 to abut stop 9. Wood fibers 10 in sample 1 are shown running parallel to the length of the sample and perpendicular to the direction of the corrugations.

It will be understood that the drawing is merely for illustration of the relationship among the various elements and has not been drawn to scale.

I claim:

1. A process for determining the crush strength of fluted wood fiber-based corrugated media, said process comprising:

a. forming corrugations in a sample of wood fiber-based medium exhibiting a rectangular shape and a pair of short edges and a pair of long edges and having the fibers of said medium running substantially parallel to said long edges;

b. placing the corrugated sample horizontally across a gap of about 0.7 to about 1 mm between a first sample holder and a second sample holder wherein each of the sample holders comprises a corrugated upper jaw in close mating relationship with both a corrugated bottom jaw and the corrugations in said sample;

c. securing said sample in said first holder and said second holder;

d. applying a horizontal crushing force on said sample by forcing one of said sample holders to move relatively toward the other sample holder; and e. measuring the force required to cause crushing failure in said sample.

2. A process as in claim 1 wherein the placing step further comprises placing the corrugated sample between parallel, vertically extending stop surfaces which run the entire length of said sample.

3. A process according to claim 1 wherein the applying step comprises applying a horizontal crushing force of about 30 to about 130 psi.

* * * * *